United States Patent [19]

Ibo et al.

[11] Patent Number: 5,755,796
[45] Date of Patent: May 26, 1998

[54] PROSTHESIS OF THE CERVICAL INTERVERTEBRALIS DISK

[76] Inventors: Ivo Ibo, Via Aganoor .26, 35123 Padua; Emilio Pierotto, Via M. Melette, 36016 Thiene, both of Italy

[21] Appl. No.: 659,274

[22] Filed: Jun. 6, 1996

[51] Int. Cl.⁶ ........................................................ A61F 2/44
[52] U.S. Cl. ............................... 623/17; 623/18; 606/61
[58] Field of Search .............................. 623/17, 18, 21, 623/23; 606/60, 61, 71

[56] References Cited

U.S. PATENT DOCUMENTS

| | | | |
|---|---|---|---|
| 5,376,125 | 12/1994 | Winkler | 623/23 |
| 5,425,773 | 6/1995 | Boyd et al. | 623/17 |
| 5,425,779 | 6/1995 | Schlosser et al. | 623/23 |
| 5,480,401 | 1/1996 | Navas | 623/17 |
| 5,540,688 | 7/1996 | Navas | 623/17 |
| 5,562,737 | 10/1996 | Graf | 623/17 |

*Primary Examiner*—Paul B. Preuilic
*Attorney, Agent, or Firm*—McAulay Fisher Nissen Goldberg & Kiel, LLP

[57] ABSTRACT

A prosthesis for a cervical intervertebral disk for fastening two contiguous vertebrae, including two components, one of which is for attachment to a first contiguous vertebrae and a second is for attachment to a second of the two contiguous vertebrae, the one component comprises a hollow box frame and includes a first end having first attachment for attaching the first end to one vertebra for holding the first attachment thereto and a connection at a second end for receiving a connector coupled with the second component, the second component comprises a first end part for attachment to the other vertebra to the second vertebra for holding the second component thereto, and a second end part having the connector connected with the first end part to permit movement between the connector and the connection.

20 Claims, 3 Drawing Sheets

PROSTHESIS OF THE CERVICAL INTERVERTEBRALIS DISK

BACKGROUND OF THE INVENTION

1. Field of the Invention

This invention is concerned with a prosthesis for a cervical intervertebral disk. More particularly, the invention is concerned with pin joint sets to fasten two plates on two contiguous vertebrae.

2. Description of the Prior Art

In neurosurgery operations on herniated disks or cervical arthrosis, emptying out of the intervertebral disk is required, and its volumetric reintegration with a bone fragment taken from another part of the same patient. This operation causes, for an osseous fusion, a stiffening of the adjacent vertebrae and a consequent reduction of the neck mobility.

Summary of the Invention

An object of the invention is to overcome or alleviate the aforedisclosed problems.

Accordingly, the prosthesis according to the invention proposes to solve the above stated problem with a prosthesis which provides a joint junction placed between a higher vertebra and a lower one for restoring and reconstructing mobility functions of the cervical intervertebralis disk under operation. In particular, a disk prosthesis with two components joined by a joint is provided.

To these ends, the present invention consists in a prosthesis for a cervical intervertebral disk for fastening two contiguous vertebrae, including two components, a first component is provided for attachment to a first of two contiguous vertebrae and a second component for attachment to a second of two contiguous vertebrae, the first component comprises a hollow box frame including a first end having a first attachment means for attaching the first end to a first means provided on the first vertebra for holding the first attachment means thereto, and connection means at a second end for receiving a connector means coupled with the second component, the second component comprises a first end part including second means for attachment to a second of the two contiguous vertebrae to second means on the second vertebra for holding thereto the second attachment means, an a second end part having the connector means connected with the first end part to permit movement between the connector means and the connection means.

The first means on the first vertebra includes openings and the first attachment means includes a pair of fastening holes alignable with the openings, and screw means for each of the pair of fastening holes for attachment of the first attachment means to the first vertebra. The first attachment means includes a lower transverse plate having an L-shaped surface with one leg of the L-shaped surface fitting within a chase seat on the first vertebra and another leg of the L-shaped surface being substantially orthogonal to the one leg, the fastening holes being in the other leg for holding thereof to the second vertebra below the chase seat and the one leg laying in the chase seat.

The second attachment means includes a transverse end plate provided with two clamping holes aligned with two holes on a wall on the second vertebra, and the screw means includes screws which pass through the clamping holes and are receivable in the two second vertebrae holes for clamping the transverse end plate to the second vertebra.

The hollow box frame is provided with an upward front opening on an oblique wall and carries on an outside thereof a lower transverse plate projection forming the first end and the first attachment means, and the connection means includes a ring mouth centrally situated on an upwardly slanted wall as an access to a conical cradle and leads to a spherical holding seat through a cylindrical tract for receiving the connector means.

The connection means includes a spherical holding seat formed from a polyethylene anti-friction material positioned in the hollow box frame, and the connector means includes a spherically-shaped body receivable within the spherical holding seat for articulation of the first and the second components relative to each other, and the second attachment means is connected with the spherically-shaped body.

The connection means includes a conical cradle connected with the spherical holding seat by a cylindrical tract, and the connector means includes an inwardly bent throttling part positioned in the cylindrical tract and with an opening conical tract; the conical cradle regulates movement of the bent throttling part, and the first end part extending from the bent throttling part.

According to another feature of the invention, the hollow box frame includes a cylindrically-shaped opening and the second end part of the second component includes a cylindrical member receivable in the cylindrically-shaped opening, and retention means on the hollow box frame and the cylindrical member for holding thereof together. The retention means includes a pair of first half seats on the interior of the hollow box means on a wall of the cylindrically shaped opening, a pair of second half seats on the cylindrical member aligned with and complementary to the first pair of half seats to form two full seats and two release pins positioned between each pair of the first and the second half seat for locking the cylindrical body to the hollow box means. The plastic body includes a spherically shaped holding seat having an intermediate cylindrical tract and a conical cradle opening to a slanted exit opening to provide for the application of the end part for receiving a spherical body provided with a throttling element and a plate shaped end.

In order that the invention will be more clearly understood and readily carried into effect, the same will now be described in connection with the accompanying drawings.

DETAILED DESCRIPTION OF THE REFERRED EMBODIMENTS

Figure 1:
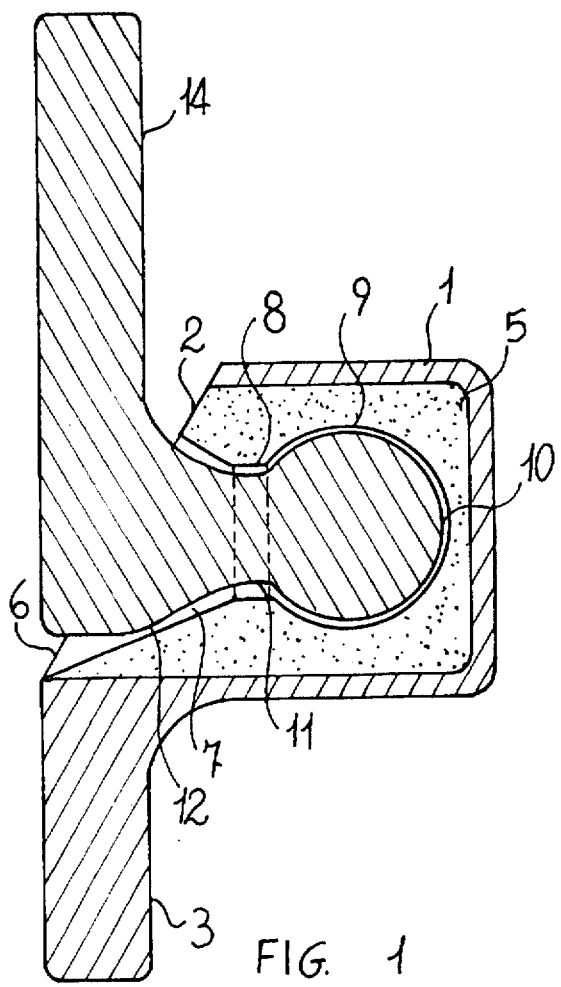
FIG. 1 is a longitudinal sectional view taken on line A—A[1] of FIG. 4 of a prosthesis according to the invention for joining two contiguous cervical vertebrae.
Figure 2:
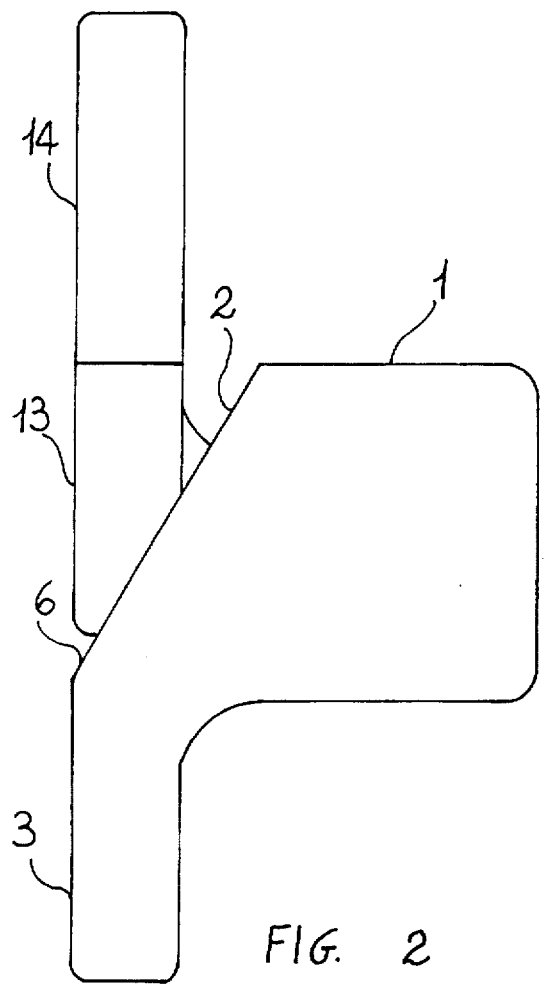
FIG. 2 is a longitudinal side view of the prosthesis shown in FIGS. 1 and 4, illustrating one outside view.
Figure 3:
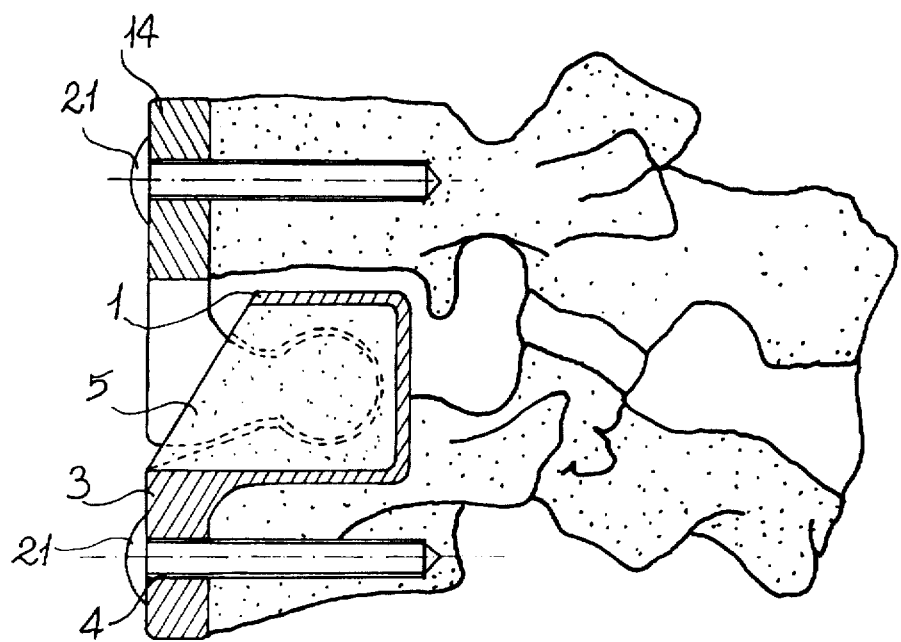
FIG. 3 is a sectional view taken on line B—B[1] of FIG. 4 showing the prosthesis joining two contiguous cervical vertebrae.
Figure 4:
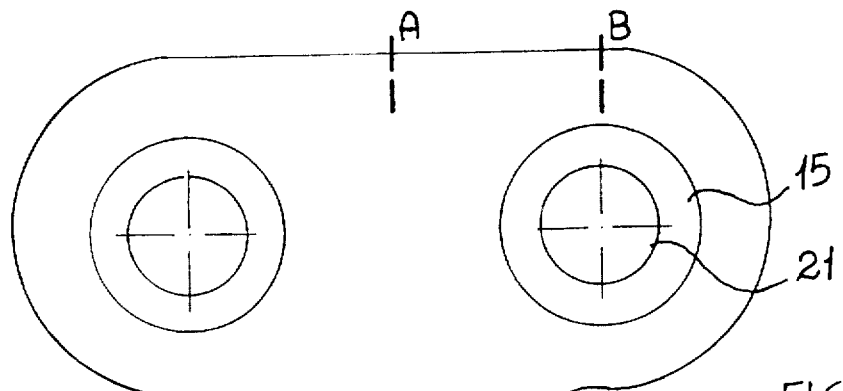
FIG. 4 is a front view of the prosthesis shown in FIGS. 1 and 2, with details of the two contiguous cervical vertebrae to be joined omitted.

Referring now more particularly to the accompanying drawings which show the best mode presently contemplated for carrying out the invention, and to FIGS. 1 to 5 which show one embodiment of the invention in which the prosthetic device comprises a hollow parallelepipedally-shaped box frame 1 forming a first component for connection to one or a lower-vertebra, (see FIGS. 1 to 3) with an upwardly inclined or slanted front opening on an oblique wall 2 and having a lower transverse plate-shaped projection 3 for connection to the one or lower vertebra, and provided with a pair of fastening holes or openings 4 (see FIG. 3), and a spherically-shaped body 10 connected with end plate 14 forming a second component.

Box frame 1 is fitted with an anti-friction material, such as polyethylene 5 to form a holding seat for spherically-shaped body 10 to provide for limited constraint for joint movement. The holding seat comprises an entry portion in the form of a ring mouth 6, on the upwardly inclined or slanted wall formed by the oblique wall 2 to provide for an access into a conical cradle proximate to the ring mouth, which in turn leads to a cylindrical tract 8 formed by a narrow cylindrical portion and then in turn which leads to a spherical holding seat 9 which increases from the diameter of cylindrical tract 8. Cylindrical tract 8 has a diameter less than the diameter of spherical holding seat 9 and is equal to the narrowest diametrical extent of the entrance to spherical holding seat 9 and the entrance to a conical cradle 7. The spherical holding seat 9 has a sliding regulated by the confines of the holding seat itself.

The second component of the prosthetic device which cooperates with the first component comprises spherically-shaped body 10, and fits within the enclosure formed by the spherical holding seat 9 of the first component. Spherically-shaped body 10 is connected with a terminal part of a diameter less than the diameter of cylindrical tract 8 and passes through an opening conical tract 12 and conical cradle 7. Spherically-shaped body 10 has its movement in spherical holding seat 9 regulated by conical cradle 7 and opening conical tract 12 as well as its relative movement with respect to plate-shaped projection 3. The outer circumferential surface configuration of inwardly bent throttling member 11 has a portion of its outer surface portion complementary to the outer circumferential surface of cylindrical tract 8 as defined by surface portion formed by polyethylene 5 surrounding the inwardly bent throttling member 11. The outer surface of conical cradle 7 for a portion thereof is substantially complementary to the outer surface portion of opening conical tract 12.

A central post 13 extending from inwardly bent throttling member 11 has one end joined to a transverse end plate 14 for connection to another or upper vertebra (see FIG. 3), and has its other end joined with spherical body 10 through the inwardly bent throttling member 11. Transverse end plate 14 is provided clamping holes or openings 15 (see FIG. 3) for connection to the upper vertebra and together with plate shaped projection 3 underneath end plate 14 form the joining portions of the prosthetic device to upper vertebra wall 19.

Figure 5:
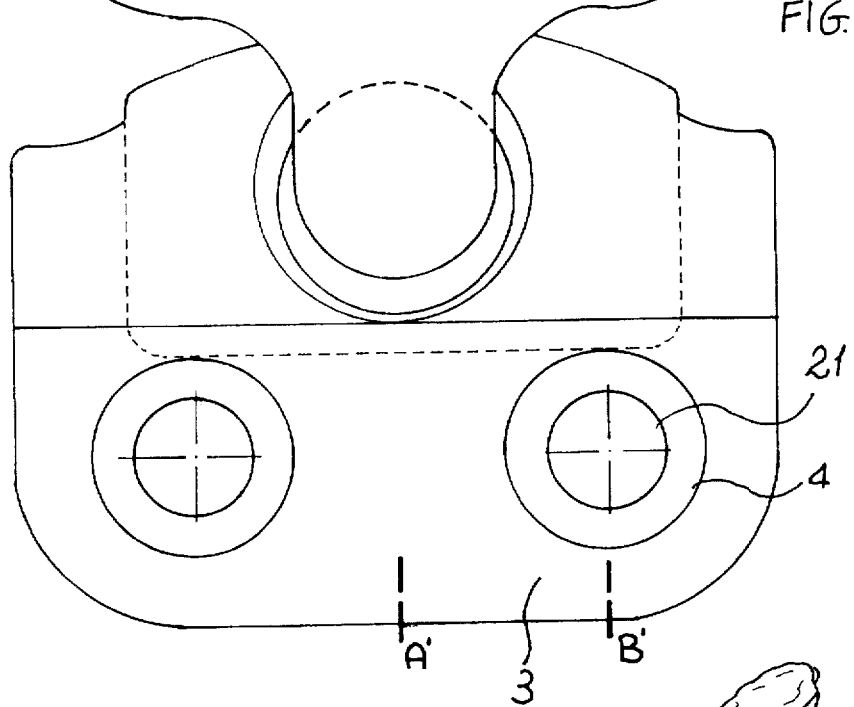
FIG. 5 is an ideographic representation of two contiguous cervical vertebrae which are to be joined together and spaced from each other, illustrating connections on each of the vertebrae to which the prosthetic device is to be joined, and showing areas provided onto which the prosthesis is to be set in place for joinder of two cervical vertebrae; and showing the provision of a particular realization the prosthesis for the cervical intervertebralis disk with a holding part with two release components to allow the substitution of components for the prosthesis position.
Figure 6:
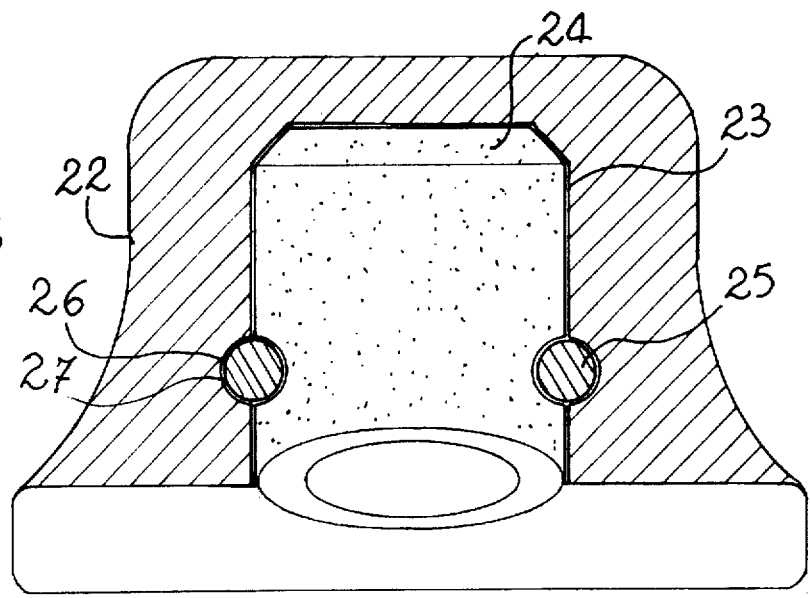
FIG. 6 is a schematic showing partially in sections of a detail of the prosthesis shown in FIGS. 1 to 5 with the cervical vertebrae omitted and portions of the prosthesis not shown, but showing a box frame and a plastic body received and seated in the box frame under holding conditions.

Reference is now made to FIG. 5, which shows the upper and lower vertebra juxtaposed to each other. To provide for the connections or joinder of the prosthetic device to each vertebra, one or the lower vertebra is provided on a side wall 16 thereof with holes 17 and above the holes 17 with an upper laying seat 18 in the form of a chase to receive hollow box frame 1 with plate shaped projection 3 having the fastening holes 4 aligned with holes 17 on wall 16.

The other or upper vertebra is provided with wall 19 having holes which are aligned with clamping holes 15 on end plate 14.

In order to join the two contiguous vertebrae, hollow box 1 has an L-shaped portion with a longer leg portion fitting into chase 18 and a shorter leg portion which is placed against wall 16 so that one part of the disk prosthesis is applied by positioning the hollow box frame 1 into the laying seat 18 and the transverse plate-shaped projection 3 on the wall 16 of the lower vertebra and positioning end plate 14 on wall 19 of the upper vertebra.

Screws 21 (see FIG. 3) are provided to connect plates 3 and 14 to their associated vertebrae. These screws 21 pass through holes 4 and 15 for joinder with the holes or openings 17 and 20 in the lower and upper vertebrae, respectively.

Reference is made to FIGS. 6 to 9 which show another embodiment of the invention, in which hollow box frame 22 is provided with two release components forming a holding part. Box frame 22 has a central laying or receiving seat 23 for receiving a cylindrical member or body 24 formed plastic material and provided with a clearance between the outer surface portion of body 24 and the inner surface portion of hollow body or hollow box frame 22 forming the central laying seat 23.

A pair of pins 25 (see FIG. 6) are provided which fit in diametrically opposite ducts formed by half seats 26 (see FIGS. 6, 8 and 9) on plastic body 24 and half seats 27 formed on inner central opening of hollow box frame 22.

Figure 7:
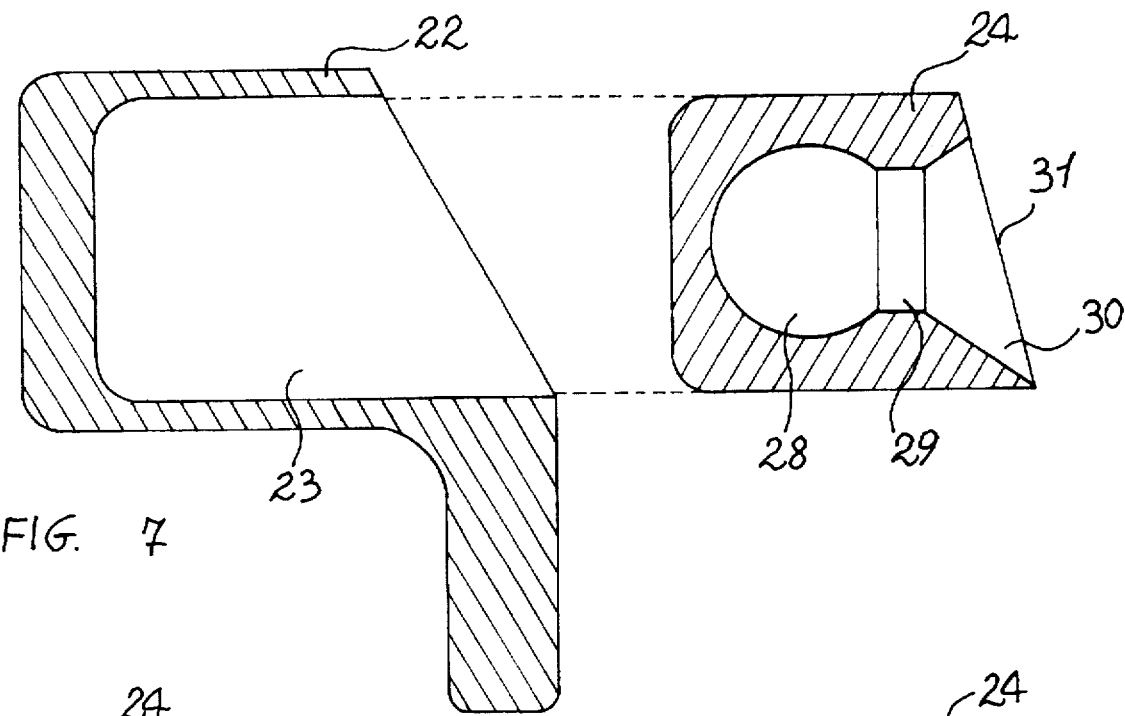
FIG. 7 is a longitudinal cutaway view of the box frame and plastic body in position for insertion of the plastic body into the box frame.
Figure 8:
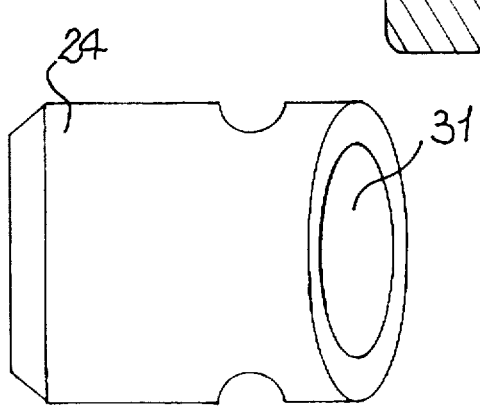
FIG. 8 is a schematic side view of the plastic body.
Figure 9:
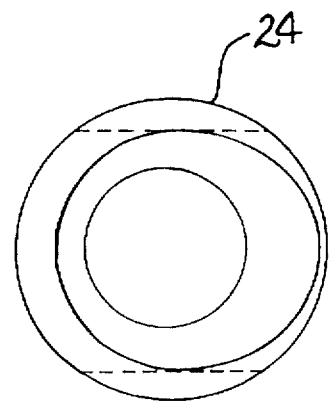
FIG. 9 is a front view of the plastic body.

Plastic body 24 in a manner similar to holding seat 9 in FIG. 1 is provided with a holding seat 28 connected with a narrowed cylindrical portion forming an intermediate cylindrical tract 29 which opens into conical cradle 30 and is reached through opening 31 which is upwardly slanted to permit the application of an analogous part for the setting in of spherical body 10 with inwardly bent throttling 11 and a plate-shaped end 14. In this version, a cutaway transverse view of box frame 22 with the plastic body 24 under holding conditions in seat 23 is shown. A longitudinal cutaway view of the box frame 22 and of the plastic body 24 in their insertion position is shown in FIG. 7. While there has been shown what is considered to be the preferred embodiments of the invention, it will be obvious to those skilled in the art that various changes and modifications may be made therein without departing from the scope of the invention.

We claim:

1. A prosthesis for a cervical intervertebral disk for fastening two contiguous vertebrae, comprising:

a first component for attachment to a first of two contiguous vertebrae and a second component for attachment to a second of two contiguous vertebrae;

said first component comprising a hollow box frame including a first end having first attachment means for attaching said first end to first means provided on a first of the two contiguous vertebrae for holding said first attachment means thereto, said hollow box frame being provided with an upward front opening on an oblique wall and carries on an outside thereof a lower transverse plate projection forming said first end and said first attachment means, and connection means at a second end for receiving a connector means coupled with said second component;

said second component comprising a first end part including second means for attachment to a second of said contiguous vertebrae to second means on the second vertebra for holding thereto said second attachment means, and a second end part having said connector means connected with said first end part to permit movement between said connector means and said connection means; and said connection means includes a ring mouth centrally situated on an upwardly slanted wall as an access to a conical cradle and leads to a spherical holding seat through a cylindrical tract for receiving said connector means.

2. The prosthesis as claimed in claim 1, wherein said first means on the first vertebra includes openings and said first attachment means includes a pair of fastening holes, and including screw means for each of said pair of fastening holes for attachment of said first attachment means to the first vertebra.

3. The prosthesis as claimed in claim 2, wherein said first attachment means includes a lower transverse plate having an L-shaped surface with one leg of said L-shaped surface fitting within a chase seat on the first vertebra and another leg of said L-shaped surface being substantially orthogonal to said one leg, said fastening holes being in said other leg for holding thereof to said second vertebra below said chase seat and said one leg laying in said chase seat.

4. The prosthesis as claimed in claim 1, wherein said second attachment means includes a transverse end plate provided with two clamping holes aligned with two holes on a wall on said second vertebra, and said screw means includes screws which pass through said clamping holes and receivable in said two second vertebrae holes for clamping said transverse end plate to said second vertebra.

5. The prosthesis as claimed in claim 1, wherein said connection means includes a spherical holding seat formed from a polyethylene anti-friction material positioned in said hollow box frame, and said connector means includes a spherically-shaped body receivable within said spherical holding seat for articulation of said first and said second components relative to each other and said second attachment means being connected with said spherically-shaped body.

6. The prosthesis as claimed in claim 5, wherein said connection means includes a conical cradle connected with said spherical holding seat by a cylindrical tract, and said connector means includes an inwardly bent throttling member positioned in said cylindrical tract and with an opening conical tract, said conical cradle regulating movement of said bent throttling member, and said first end part extending from said inwardly bent throttling member.

7. The prosthesis as claimed in claim 1, wherein said hollow box frame includes a cylindrically-shaped opening and said second end part of said second component includes a cylindrical member receivable in said cylindrically-shaped opening, and retention means on said hollow box frame and said cylindrical member for holding thereof together.

8. The prosthesis as claimed in claim 7, wherein said retention means includes a pair of full half seats on said interior of said hollow box frame on a wall of said cylindrically shaped opening, a pair of second half seats on said cylindrical member aligned with and complementary to said first pair of half seats, and two release pins positioned between each pair of said first and said second half seat for locking said cylindrical body to said hollow box means.

9. The prosthesis as claimed in claim 7, wherein said cylindrical body includes a plastic body having a spherically shaped holding seat having an intermediate cylindrical tract and a conical cradle opening to a slanted exit opening to provide for the application of said end part for receiving a spherical body provided with a throttling member and a plate shaped end, and said spherically shaped holding seat receives said spherical body.

10. The prosthesis as claimed in claim 7, wherein said first attachment means includes a lower transverse plate having an L-shaped surface with one leg of said L-shaped surface fitting within a chase seat on the first vertebra and another leg of said L-shaped surface being substantially orthogonal to said one leg, said fastening holes being in said other leg for holding thereof to said second vertebra below said chase seat and said one leg laying in said chase seat.

11. The prosthesis as claimed in claim 7, wherein said cylindrical member includes a spherical holding seat formed from a polyethylene anti-friction material positioned in said hollow box frame, and said connector means includes a spherically-shaped body receivable within said spherical holding seat for articulation of said first and said second components relative to each other and said second attachment means being connected with said spherically-shaped body.

12. The prosthesis as claimed in claim 11, wherein said cylindrical body includes a conical cradle connected with said spherical holding seat by a cylindrical tract, and said connector means includes an inwardly bent throttling member positioned in said cylindrical tract and with an opening conical tract, said conical cradle regulating movement of said bent throttling member, and said first end part extending from said inwardly bent throttling member.

13. The prosthesis as claimed in claim 7, wherein said second attachment means includes a transverse end plate provided with two clamping holes aligned with two holes on a wall on said second vertebra, and said screw means includes screws which pass through said clamping holes and receivable in said two second vertebrae holes for clamping said transverse end plate to said second vertebra.

14. The prosthesis as claimed in claim 12, wherein said second attachment means includes a transverse end plate provided with two clamping holes aligned with two holes on a wall on said second vertebra, and said screw means includes screws which pass through said clamping holes and receivable in said two second vertebrae holes for clamping said transverse end plate to said second vertebra.

15. A cervical intervertebral disk prosthesis for fastening two contiguous vertebrae, comprising:

a first component for attachment to a first of two contiguous vertebrae and a second component for attachment to a second of two contiguous vertebrae;

said first component comprising a box frame including a first end having first attachment means for attaching said first end to first means provided on a first of the two contiguous vertebrae for holding said first attachment means thereto, and connection means at a second end for receiving a connector coupled with said second component;

said second component comprising a first end part including second means for attachment to a second of said two contiguous vertebrae to second means on the second vertebra for holding thereto said second attachment means, and a second end part having said connector means connected with said first end part to permit movement between said connector and said connection means; and said connector including a ring mouth centrally situated on an upwardly slanted wall as an access to a conical cradle and leading to a spherical holding seat through a cylindrical tract for receiving said connector.

16. The prosthesis as claimed in claim 15, wherein said box frame is a hollow box provided with an upward front opening on an oblique wall and carries on an outside thereof a lower transverse plate projection forming said first end and said first attachment means.

17. The prosthesis as claimed in claim 15, wherein said conical cradle is connected with a spherical holding seat by a cylindrical tract, said connector includes a spherically-shaped body receivable within said spherical holding seat for articulation of said first and said second components relative to each other, and an inwardly bent throttling member positioned in said cylindrical tract and with an opening conical tract, said conical cradle regulating movement of said bent throttling member, and said first end part extending from said inwardly bent throttling member.

18. A prosthesis for a cervical intervertebral disk for fastening two contiguous vertebrae, comprising:

a first component for attachment to a first of two contiguous vertebrae and a second component for attachment to a second of two contiguous vertebrae;

said first component comprising a frame including a first end having first attachment means for attaching said first end to first means provided on a first of the two contiguous vertebrae for holding said first attachment means thereto, and connection means at a second end for receiving a connector coupled with said second component, said frame being further provided with an upward front opening on an oblique wall and carrying on an outside thereof a lower transverse plate projection forming said first end and said first attachment means; said frame is a hollow box member provided with an cylindrically-shaped opening and said second end part of said second component includes a cylindrical body receivable in said cylindrically-shaped opening; and said second component comprising a first end part including second attachment means to a second of said two contiguous vertebrae to second means on the second vertebrae for holding thereto said second attachment means, and a second end part having said connector means connected with said first end part to permit movement between said connector and said connection means.

19. The prosthesis as claimed in claim 18, including retention means associated with said hollow box frame and said cylindrical member for holding thereof together, said cylindrical body including a plastic body having a spherically-shaped holding seat for receiving a spherical body provided with a throttling member and a plate-shaped end, said spherically-shaped holding seat having an intermediate cylindrical tract and a conical cradle opening to a slanted exit opening to provide for the application of said end part for receiving said spherical body.

20. The prosthesis as claimed in claim 19, wherein said connection means includes a ring mouth centrally situated on an upwardly slanted wall as an access to the conical cradle and leading to the spherically-shaped holding seat through a cylindrical tract for receiving said connector.

* * * * *